(12) United States Patent
Bentley et al.

(10) Patent No.: US 10,485,805 B2
(45) Date of Patent: *Nov. 26, 2019

(54) FINAFLOXACIN FOR USE IN THE TREATMENT OF URINARY TRACT INFECTIONS

(71) Applicant: MerLion Pharmaceuticals Pte. Ltd., Singapore (SG)

(72) Inventors: Christine Bentley, Schildow (DE); Carsten Fischer, Berlin (DE); Mark Lückermann, Berlin (DE); Andreas Vente, Berlin (DE); Sven-Eric Wohlert, Berlin (DE)

(73) Assignee: MerLion Pharmaceuticals Pte. Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 15/541,543

(22) PCT Filed: Nov. 10, 2015

(86) PCT No.: PCT/IB2015/058660
§ 371 (c)(1),
(2) Date: Jul. 5, 2017

(87) PCT Pub. No.: WO2016/110754
PCT Pub. Date: Jul. 14, 2016

(65) Prior Publication Data
US 2017/0354661 A1    Dec. 14, 2017

(30) Foreign Application Priority Data

Jan. 6, 2015 (DE) .................. 10 2015 100 068

(51) Int. Cl.
*A61K 31/5383* (2006.01)
(52) U.S. Cl.
CPC ............... *A61K 31/5383* (2013.01)
(58) Field of Classification Search
CPC ....... A61K 31/5383; A61P 13/00; A61P 13/02
See application file for complete search history.

(56) References Cited

U.S. PATENT DOCUMENTS 8,536,167 B2   9/2013   Stroman et al.

FOREIGN PATENT DOCUMENTS

| WO | WO-2014088838 A1 * | 6/2014 | ......... A61K 31/5383 |
| WO | WO-2016071784 A1 * | 5/2016 | ........... A61K 9/0019 |

OTHER PUBLICATIONS

MerLion Pharmaceuticals GmbH ("Finafloxacin for the Treatment of cUTI and/or Acute Pyelonephritis"; ClinicalTrials.gov; Clinical Trials Identifier: NCT01928433; Aug. 23, 2013; https://clinicaltrials.gov/archive/NCT01928433/2013_08_23; accessed Mar. 7, 2018 (Year: 2013).*
Sigma (Tris(hydroxymethyl)aminomethane; Tris; Technical Bulletin No. 106B; https://www.sigmaaldrich.com/content/dam/sigma-aldrich/docs/Sigma/Bulletin/1/106bbul.pdf; 1996; accessed Mar. 7, 2018 (Year: 1996).*
International Search Report for corresponding PCT/IB2015/058660 dated Jan. 12, 2016, three pages.
Written Opinion of the International Searching Authority for corresponding PCT/IB2015/058660 dated Jan. 12, 2016, seven pages.
"(Jan. 8, 2015) Finafloxacin background (phase II cUTI trial & drug characteristics)" www.merlionpharma.com/?q=node/2, two pages.
Peterson et al., "A Double-Blind, Randomized Comparison of Levofloxacin 750 mg Once-Daily for Five Days With Ciprofloxacin 400/500 mg Twice Daily for 10 Days for the Treatment of Complicated Urinary Tract Infections and Acute Pyelonephritis," Urology 71 (1), 2008, pp. 17-22.
Wagenlehner et al., "Urinary Pharmacokinetics and Bactericidal Activity of Finafloxacin (200 and 800 mg) in Healthy Volunteers Receiving a Single Oral Dose," Chemotherapy 2011, 57, pp. 97-107.

* cited by examiner

*Primary Examiner* — Timothy P Thomas
(74) *Attorney, Agent, or Firm* — Rankin, Hill & Clark LLP

(57) ABSTRACT

It was found that finafloxacin eradicates pathogens from patients suffering from bacterial infections like urinary tract infections and pyelonephritis more quickly than other fluoroquinolones regularly used for the treatment of these patients. Due to the efficacy of finafloxacin reduced treatment durations without increasing the daily dosage of finafloxacin and at the same time no or shorter stays in hospital are realizable, thus improving patient convenience and significantly lowering the costs of hospitalization and treatment. Reduced hospitalization periods do also clearly reduce the risk of nosocomial infections and of generating drug-resistant strains through extended therapy. The inventive treatment regimens comprise an oral finafloxacin administration for 1-5 days or a parenteral finafloxacin administration for 1-5 days for use in the treatment of a complicated urinary tract infection or pyelonephritis. However, a prior short parenteral administration of finafloxacin (e.g. 3 days) in combination with an oral administration (e.g. 2 days) may be applied, if necessary in case of really severe infections. The present invention further relates to a novel treatment regime for the treatment of uncomplicated UTI whereby a single oral finafloxacin dose is considered to be sufficient to effectively treat patients with uncomplicated UTI.

7 Claims, No Drawings

FINAFLOXACIN FOR USE IN THE TREATMENT OF URINARY TRACT INFECTIONS

BACKGROUND OF THE INVENTION

This invention relates to the use of improved regimens for the administration of finafloxacin for the treatment of uncomplicated and complicated urinary tract infections (UTIs) and pyelonephritis.

Finafloxacin is a novel fluoroquinolone and combines essential features required to successfully treat bacterial infections: good activity against Gram positive, Gram negative and anaerobic pathogens. Finafloxacin (INN International Nonproprietary Name) is an antibiotic of the class of the quinolone carboxylic acids of the following formula: (−)-8-cyano-1-cyclopropyl-6-fluoro-7-[(4aS,7aS)-hexahydropyrrolo[3,4-B]-1,4-oxazin-6(2H)-yl]-4-oxo-1,4-dihydroquinoline-3-carboxylic acid. Finafloxacin has been described as useful in the treatment of *H. pylori* infections (EP0946176) or of ophthalmic, otic, or nasal infections (U.S. Pat. No. 8,536,167). Finafloxacin and derivatives thereof can be synthesized according to the methods described in WO 98/26779 by Matzke et al., the contents of which are herein incorporated by reference in their entirety.

In vitro and in vivo microbiological assessments show that finafloxacin is effective in animal infection models. The high activity of finafloxacin at the site of infection is thereby attributed, in part, to its unique enhanced antibacterial activity at pH values below neutral.

The increased activity of finafloxacin in an acidic environment was found to be exactly opposite to that of all marketed quinolones, which substantially reduced activity under these conditions. Therefore finafloxacin appears to be an excellent medication in all indications associated with a low pH environment. The spectrum of antibacterial activity of finafloxacin covers the vast majority of pathogens predominant in UTIs, intra-abdominal infections, skin infections and other indications.

The European Association of Urology advises specific regimens for the treatment of the various forms of UTIs. For mild and moderate cases of acute uncomplicated UTI the guidelines of the European Association of Urology (2014) recommends an oral therapy with various antibiotics for 3-7 days, amongst them regimens with fluoroquinolones for 3 days. For mild and moderate cases of acute uncomplicated pyelonephritis an oral therapy of 5-14 days with different antibiotics is recommended, amongst them regimens with fluoroquinolones for 7-10 days. For complicated UTIs the guidelines advise the treatment for 7-21 days with an initial parenteral therapy for hospitalized patients which can subsequently be switched to an oral treatment.

Pathogens exposed to the nosocomial environment develop resistances through mutation due to selective pressure by antibiotic or antiseptic medications used and leading experts to state that nosocomial UTIs comprise perhaps the largest institutional reservoir of nosocomial antibiotic resistant pathogens. UTIs are among the most prevalent infectious diseases in ambulatory and hospitalized populations, with a substantial financial burden on the society. Up to 40% of women will develop a UTI at least once in their lifetime, and a significant number of them will have recurrences. In the USA the treatment of UTI accounts for about 15% of all community-prescribed antibiotics and every year UTIs result in more than 100,000 hospital admissions. UTIs are also considered to be responsible for at least 40% of all nosocomial infections, most of which are being catheter associated.

It is therefore medicinally desirable to avoid a hospital treatment or at least to reduce the length of the hospital stay of patients suffering from UTIs, and accordingly a need for drugs giving the physicians that possibility.

Thus, there is the need for treatment regimens with reduced treatment durations in order to minimize the likelihood of developing resistances due to selective pressure by antibiotic medications. In case of necessary hospitalizations shorter stays in hospital should reduce the risk of nosocomial infections and of generating drug-resistant strains through extended therapy. Ideally, a parenteral therapy for hospitalized patients should be avoided. Therefore, in case of uncomplicated UTI shorter treatment periods than the recommended 3-7 days would be beneficial. In case of complicated UTI and pyelonephritis reduced treatment durations of less than 7 days would have clear advantages. Especially treatment regimens without the necessity of parenteral therapy are preferable because any hospitalization with the risk of nosocomial infections could be avoided.

SHORT DESCRIPTION OF THE INVENTION

The present invention generally relates to finafloxacin for use in the treatment of UTIs and pyelonephritis. Surprisingly, it was found that finafloxacin eradicates pathogens from patients more quickly than other fluoroquinolones regularly used for the treatment of these patients. This superior efficacy of finafloxacin allows in general shorter treatment periods. Such shorter treatment periods are in particular achievable without increasing the daily dosage of finafloxacin.

The present invention specifically relates to novel treatment regimens for the treatment of complicated UTI and pyelonephritis. Such novel treatment regimens comprise the preparation of finafloxacin for an oral administration for 2-5 days or for a parenteral administration for 1-5 days without increasing the daily dosage of finafloxacin. This is a considerably reduced period of time for the treatment of complicated UTI. A prior short parenteral administration of finafloxacin in combination with an oral administration might be administered in case of severe infections. In such case an embodiment of the invention suggests an intravenous administration for 1-3 days prior to an oral administration for 1-2 days. The present invention further relates to a novel treatment regime for the treatment of uncomplicated UTI whereby finafloxacin is prepared for a 1 or 2 day treatment regimen in the form of an oral administration or a parenteral administration. A single oral finafloxacin dose is considered to be sufficient to effectively treat patients with uncomplicated UTI and is thus especially preferred.

DETAILED DESCRIPTION OF THE INVENTION

The present invention comprises finafloxacin or a pharmaceutically acceptable salt, derivative, enantiomer, or hydrate thereof. Finafloxacin (INN International Nonproprietary Name) is an antibiotic of the class of the quinolone carboxylic acids of the following formula: (−)-8-cyano-1-cyclopropyl-6-fluoro-7-[(4aS,7aS)-hexahydropyrrolo[3,4-b]-1,4-oxazin-6(2H)-yl]-4-oxo-1,4-dihydroquinoline-3-carboxylc acid.

A preferred salt in embodiments of the present invention is finafloxacin monohydrochloride. Diastereomerically and enantiomerically pure finafloxacin is also preferred for use in embodiment of the present invention. As used herein, the term "finafloxacin" is intended to encompass finafloxacin and its pharmaceutically acceptable salts, derivatives, enantiomers, or hydrates as well as pharmaceutically acceptable compositions comprising finafloxacin. The phrase "pharmaceutically acceptable" is art-recognized and refers to salts, compositions, polymers and other materials and/or dosage forms which are suitable for use in contact with the tissues or human beings and animals without excessive toxicity, irritation, allergic response, or other problem or complications, commensurate with a reasonable benefit/risk ratio as determined by of ordinary skill in the art.

The present invention relates to finafloxacin for use in the treatment of a complicated UTI or pyelonephritis. The novel treatment regimen provides an oral administration for 1-5 days. The exact duration, i.e. 1 day, 2 days, 3 days, 4 days or 5 days, has to be set forth in accordance with the seriousness of the UTI or pyelonephritis. These short incubation periods are made possible due to the surprising fast and effective eradication of pathogens. Non-clinical and clinical examples show that even such short treatment regimens of finafloxacin can be successfully used to cure patients from complicated UTIs or pyelonephritis.

Due to this inventive treatment regimen comprising an oral administration for just 1-5 days, a hospitalization is in many cases no longer required. An exposure of pathogens to a nosocomial environment can thus be avoided and therefore also the general development of resistances through mutation due to selective pressure by antibiotic or antiseptic medications used. An oral administration without the necessity of a hospitalization is also a clear advantage for the patients per se in comparison to the commonly used treatment regiments for complicated UTIs advising a treatment for 7-21 days with an initial parenteral therapy in a hospital.

In an embodiment, the present invention provides a treatment duration of 3 days which represents a significant reduction against the recommended treatment period of at least 7 days. Such reduced administration period can help minimizing the likelihood to develop resistances due to selective pressure by antibiotic medications.

In case of necessary hospitalizations due to severe complicated UTIs a short stay in hospital should reduce the risk of nosocomial infections and of generating drug-resistant strains through extended therapy. Thus, the invention further relates to a short parenteral administration of 1-5 days. A parenteral administration may also be combined with an oral administration according to a further embodiment of the invention.

A preferred embodiment of the invention is a five day treatment regimen consisting of the combination of a 1-4 day parenteral administration, e.g. a 3 day parenteral administration, followed by a 1-4 day oral administration, e.g. a 2 day oral administration. Longer treatment duration does not result in better clinical success. This success was reached with the same daily finafloxacin dosages, i.e. the dosage with the shorter treatment regimen was identical to the daily finafloxacin dosage with the longer treatment period.

A 5 day treatment regimen with intravenous daily doses of 800 mg finafloxacin for 3 days followed by 2 days with 800 mg daily oral dosing showed a similar or a slightly better treatment success than a 10 day treatment regimen with intravenous daily doses of 800 mg finafloxacin for 3 days followed by 7 days with 800 mg daily oral dosing. The treatment success has been defined as the combined clinical response and microbiological response. The clinical response is defined as resolution of the symptoms of complicated UTI or pyelonephritis present at trial entry and no new symptoms developed. The microbiological response is defined as elimination or reduction of the concentration of the pathogen in the urine to a titer of $\leq 10^3$. The clinical success was determined by examinations one week after the end of the last drug intake as suggested by the "Guidance for Industry Complicated Urinary Tract Infections: Developing Drugs for Treatment" published by the U.S. Department of Health and Human Services, Food and Drug Administration, Center for Drug Evaluation and Research (CDER) in February 2012.

A longer finafloxacin treatment of 10 days according to the guidelines for the treatment of complicated UTI surprisingly does not yield better clinical results as the novel 5 day treatment regimen. On the other hand, clinical results gained with the finafloxacin treatment regimens (70.3%—5 day regimen; 67.6%—10 day regimen) were better than the clinical results (57.4%) reached with patients treated 10 days with ciprofloxacin (800 mg intravenous ciprofloxacin (400 mg doses given twice daily) for 3 days followed by a 500 mg oral dosing (two 250 mg tablets given twice daily) for 7 days).

The present invention also relates to finafloxacin for use in the treatment of uncomplicated UTIs. The novel one or two day treatment regimen may be applied in the form of an oral administration or a parenteral administration. In a further embodiment, the invention relates to finafloxacin for use in the treatment of uncomplicated UTIs and the administration of single for a one day treatment regimen. This short term treatment in comparison to the recommended oral therapy with fluoroquinolones for 3 days have been developed on the basis of the surprising finding that pathogens are be eradicated in the urine of patients suffering from uncomplicated UTIs within 2 hours after the intake of an oral formulation of finafloxacin.

The daily dose of finafloxacin used in the treatment regimens according to the invention may vary from 50-2000 mg, preferably from 200-1000 mg, most preferably from 300 mg to 800 mg. A daily dose of e.g. 800 mg finafloxacin may be represented by a composition comprising 800 mg finafloxacin in sodium chloride, Tris, hydrochloric acid and sodium hydroxide for pH adjustment and water for injection.

The applicable daily dose can be administered once a day. This once daily usage is in particular preferred with parenteral administration. However, finafloxacin may be administered at any other frequency of administration, including two times a day, three times a day, etc. If finafloxacin is used in the treatment of complicated UTIs or pyelonephritis, the daily dose is preferably 800 mg finafloxacin once daily in oral or parenteral administration. If finafloxacin is used in the treatment of uncomplicated UTIs, the daily dose used is preferably 300-800 mg finafloxacin once daily in oral administration.

In a further embodiment of the invention finafloxacin is administered to patients having a urine pH below 7. This patient group can especially benefit from a treatment with finafloxacin as the antibacterial activity of finafloxacin in the acid urinary milieu is comparable to its activity at pH-values above 7. The treatment with finafloxacin has therefore a clear advantage for patients having a urine pH below 7 in comparison to the treatment with classical fluoroquinolones like ciprofloxacin. Further, the cure rate of finafloxacin is overall higher than the ciprofloxacin cure rate. Together with the reduced treatment periods according to the invention the patient group having a urine pH lower 7 obviously profits from a treatment with finafloxacin. This clinical example shows that prescreening of patients for an acidic urine pH can be successfully used to identify patients with infections which have an elevated risk of treatment failures with other drugs, and cure them with finafloxacin.

The treatment regimens according to the invention comprise the administration of compositions comprising finafloxacin. Such compositions may be oral formulations, an intravenous solution or in general a pharmaceutically acceptable composition for parenteral application. Suitable pharmaceutically acceptable compositions for parenteral application comprise, for example and without any limitation, 1 to 6 g/l finafloxacin, 7 to 8 g/l NaCl, and 1 to 2 g/l Tris. A specific composition according to the invention is for example a composition comprising 3.2 g/l finafloxacin, 7.8 g/l NaCl, 1.21 g/l Tris. Tris is the abbreviation for 2-amino-2-hydroxymethyl-propane-1,3-diol or tris(hydroxymethyl) aminomethane. The chemical formula is $(HOCH2)3CNH2$. Tris is known as one of the mostly commonly used buffers used in biochemistry and molecular biology.

However, Tris is herein used as solubility enhancing agent. It was found that finafloxacin has a high solubility in the presence of Tris. Such solubility is significantly higher than in the presence of other substances typically used as buffers (e.g. phosphate buffer). The observed significant increase in solubility of finafloxacin in compositions comprising Tris is further advantageously accompanied by a long term stability of such solutions. Both effects lead to a completely unexpected result. Tris is therefore to be regarded as a specific tool to considerably enhance the solubility of finafloxacin in solutions. By preparing compositions comprising Tris it is possible to dissolve finafloxacin stably in such an amount therein that these compositions can effectively be used as parenteral compositions for the treatment of UTIs.

Further embodiments of the invention comprise the use of finafloxacin for the treatment of a complicated UTI or pyelonephritis, wherein finafloxacin is prepared and administered as described and defined above, and the use of finafloxacin in the manufacture of a medicament for the treatment of a complicated UTI or pyelonephritis, wherein such medicament is designed for the administration of finafloxacin as described and defined above.

Still further embodiments of the invention comprise the use of finafloxacin for the treatment of an uncomplicated UTI, wherein finafloxacin is administered as described and defined above, and the use of finafloxacin in the manufacture of a medicament for the treatment of an uncomplicated UTI, wherein such medicament is designed for the administration of finafloxacin as described and defined above.

EXAMPLES

Example 1

An overnight inoculum of $10^6$ colony forming units per ml broth adjusted to different pH values of different pathogens was exposed to finafloxacin. Bacterial growth was determined before and after 1 h of incubation.

For a *Stenotrophomonas maltophilia* clinical isolate, the number of viable bacteria in the medium was reduced by 87.4% at pH 5.2, by 99-6% at pH 6.2 and by 99.8% at pH 7.2. For *Pseudomonas aeruginosa* the number of viable bacteria in the medium was reduced by 98.6% at pH 5.2, by 99.3%% at pH 6.2 and by 99.9% at pH 7.2.

Finafloxacin caused an efficient reduction of viable pathogens in the medium. The reduction measured 1 h after incubation was at least 87.4% and up to more than 99% at pH 7.2. Finafloxacin exhibits a very broad spectrum of activity and shows a significant antibacterial activity under infection relevant conditions, i.e. at pH-values below neutral.

These results show that finafloxacin is a potent antibiotic with the potential to kill bacteria very quickly in a short incubation period.

Example 2

Patients with uncomplicated UTIs were treated with an oral dose of 300 mg finafloxacin or 250 mg of ciprofloxacin and the concentrations of the fluoroquinolone-susceptible pathogens in the urine were determined before and 2, 4 and 8 hours after intake of the drugs. (–bacterial titers below $10^3$).

TABLE

Determination of the concentration of pathogens in the urine of patients

| Patient | Drug | Bacteria per ml urine - pre dose | MIC of isolate [Cipro mg/L] | Bacteria per ml urine - hours after dose | | |
|---|---|---|---|---|---|---|
| | | | | 2 hours | 4 hours | 8 hours |
| 1 | Finafloxacin | $1.7 \times 10^7$ | 0.008 | — | — | — |
| 2 | Finafloxacin | $2.7 \times 10^5$ | 0.012 | — | — | — |
| 3 | Finafloxacin | $1.0 \times 10^6$ | 0.012 | — | — | — |
| 4 | Finafloxacin | $2.8 \times 10^5$ | 0.19 | — | — | — |
| 5 | Ciprofloxacin | $1.4 \times 10^5$ | 0.008 | — | — | — |
| 6 | Ciprofloxacin | $2.3 \times 10^6$ | 0.012 | $2.0 \times 10^3$ | — | — |
| 7 | Ciprofloxacin | $3.4 \times 10^7$ | 0.19 | $6.1 \times 10^4$ | $2.7 \times 10^3$ | — |

Finafloxacin eradicates the pathogens from patients with uncomplicated UTI more rapidly than ciprofloxacin. While 2 hours after intake of finafloxacin the bacterial titers were below $10^3$ in all analyzed samples, bacterial titers above $10^3$ were determined 2 and 4 hours after intake of ciprofloxacin in the urine of patients having high initial pre-doses.

A single oral finafloxacin dose is considered to be sufficient to treat patients with uncomplicated UTI. That is a significant advantage in comparison to the recommended oral therapy (3 days with fluoroquinolones) according to the guidelines of the European Association of Urology.

Example 3

The efficacy of a finafloxacin composition was compared to a ciprofloxacin composition in a double-blind, randomized clinical study with patients suffering from complicated UTIs or pyelonephritis.

193 patients met the inclusion criteria as specified in the "Guidance for Industry Complicated Urinary Tract Infections: Developing Drugs for Treatment" published by the U.S. Department of Health and Human Services, Food and Drug Administration, Center for Drug Evaluation and Research (CDER) in February 2012.

132 Patients with complicated UTIs and pyelonephritis were treated with an intravenous dose of 800 mg Finafloxacin once daily in sodium chloride, Tris (solubility enhancing agent), hydrochloric acid and sodium hydroxide for pH adjustment and water for injection.

61 Patients with complicated UTIs and pyelonephritis were treated with an intravenous dose of 800 mg ciprofloxacin given as 400 mg twice daily in sodium chloride, sulphuric acid and sodium hydroxide for pH adjustment, and water for injection 3 days after the start of the therapy the microbiological cure was determined. This early determination of efficacy was chosen to determine the velocity of pathogen eradication from the urinary tract. "Microbiological cure" is defined as the reduction of the concentration of the pathogen in the urine to a titer of $\leq 10^3$.

The results of the study are presented in the table below. The finafloxacin composition caused a more efficient eradication of the pathogens from the patient's urine compared to the ciprofloxacin composition.

|  | Finafloxacin composition | Ciprofloxacin composition |
| --- | --- | --- |
| Microbiological cure | 118 | 48 |
| Microbiological failure | 14 | 13 |
| Microbiological cure rate | 89.4% | 78.7% |

Example 4

The efficacy of the treatment of patients by the treatment with finafloxacin compositions for different durations was evaluated in a double-blind, randomized clinical study with patients suffering from complicated UTIs or pyelonephritis.

193 patients met the inclusion criteria for patients with complicated UTIs or pyelonephritis as specified in the "Guidance for Industry Complicated Urinary Tract Infections: Developing Drugs for Treatment" published by the U.S. Department of Health and Human Services, Food and Drug Administration, Center for Drug Evaluation and Research (CDER) in February 2012.

The 64 patients in group 1 were initially treated with intravenous daily doses of 800 mg finafloxacin in sodium chloride, Tris (solubility enhancing agent), hydrochloric acid and sodium hydroxide for pH adjustment and water for injection and after 3 days with 800 mg daily oral dosing (four 200 mg tablets). Overall treatment duration was 5 days.

The 68 patients in group 2 were initially treated with intravenous daily doses of 800 mg finafloxacin in sodium chloride, Tris (solubility enhancing agent), hydrochloric acid and sodium hydroxide for pH adjustment and water for injection and after 3 days with 800 mg daily oral dosing (four 200 mg tablets). Overall treatment duration was 10 days.

The 61 patients in group 3 were initially treated with intravenous doses of 800 mg ciprofloxacin (400 mg doses given twice daily) in sodium chloride, sulphuric acid and sodium hydroxide for pH adjustment, and water for injection and after 3 days with 500 mg oral dosing (two 250 mg tablets given twice daily). Overall treatment duration was 10 days.

17 days after the start of treatment the treatment success, i.e. the combined clinical response and microbiological response was determined. The clinical response is defined as resolution of the symptoms of complicated UTI or pyelonephritis present at trial entry and no new symptoms developed. The microbiological response is defined as elimination or reduction of the concentration of the pathogen in the urine to a titer of $\leq 10^3$.

The treatment success with patients in group 1 treated for 5 days with a finafloxacin composition was 70.3%. The treatment success with patients in group 2 treated for 10 days with a finafloxacin composition was 67.6%. The treatment success with patients in group 3 treated for 10 days with a ciprofloxacin composition was 57.4%.

This example shows that the treatment with finafloxacin for a shortened period of time (5 days) is as efficient as the treatment for a longer period of time (10 days). It also shows that a five day treatment regimen with high single daily doses (800 mg) of finafloxacin is more effective as the European standard ten day treatment regimen with ciprofloxacin. This better efficiency in treatment success was continued to be seen at the final patient visit, 24 days after the start of treatment. The treatment success with patients treated for 5 days with a finafloxacin composition was 73.34%. The treatment success with patients treated for 10 days with a ciprofloxacin composition was 55.7%.

Example 5

Urine pH of the patients with complicated UTIs or pyelonephritis was monitored and the microbiological cure rates three days after the start of the treatment in the patient groups with a urine pH below 7 were compared for a finafloxacin and a ciprofloxacin composition. The pH of the urine can easily be determined by using common pH-strip.

|  | Finafloxacin composition | Ciprofloxacin composition |
| --- | --- | --- |
| pH ≥ 7 | 91.3% | 86.7% |
| pH < 7 | 88.8% | 78.1% |

In contrast to classical fluoroquinolones the antibacterial activity of finafloxacin in the acid urinary milieu is very good. The treatment with finafloxacin has therefore a clear advantage for patients having a urine pH below 7 in comparison to the treatment with classical fluoroquinolones like ciprofloxacin. Further, the overall cure rate of finafloxacin is higher than the ciprofloxacin cure rate. Together with reduced treatment periods (Example 4) the patient group having a urine pH pf 7 or lower obviously benefits from a treatment with finafloxacin.

The invention claimed is:

1. A method of treating a complicated urinary tract infection or pyelonephritis, consisting of administering finafloxacin to a patient in need thereof for an exact treatment duration of 1, 2 or 3 days,
   wherein a daily dose of 800 mg of the finafloxacin is parenterally administered for 1, 2 or 3 days.

2. The method of claim 1, wherein finafloxacin is parenterally administered for a treatment duration of 3 days.

3. The method of claim 1, wherein the patient to which the finafloxacin is administered, has a urine pH below 7.

4. A method of treating a complicated urinary tract infection or pyelonephritis, consisting of administering parenterally a pharmaceutical composition comprising 1 to 6 g/l finafloxacin, 7 to 8 g/l NaCl, and 1 to 2 g/l Tris to a patient in need for an exact treatment duration of 1, 2 or 3 days.

5. The method of claim 4, the pharmaceutical composition comprising 3.2 g/l finafloxacin, 7.8 g/l NaCl, and 1.21 g/l Tris.

6. The method of claim 4, wherein a daily dose of 800 mg is administered.

7. The method of claim 4, wherein the patient to which the finafloxacin is administered, has a urine pH below 7.

* * * * *